United States Patent [19]

Dewhurst et al.

[11] Patent Number: 4,539,158

[45] Date of Patent: Sep. 3, 1985

[54] LIQUID DIPHENYLMETHANE DIISOCYANATE COMPOSITIONS

[75] Inventors: John E. Dewhurst, Oakdale; Jeffrey F. Dormish, Pittsburgh, both of Pa.; Richard S. Pantone, New Martinsville, W. Va.

[73] Assignee: Mobay Chemical Corporation, Pittsburgh, Pa.

[21] Appl. No.: 681,747

[22] Filed: Dec. 14, 1984

[51] Int. Cl.³ .......................................... C07C 119/048
[52] U.S. Cl. ........................ 260/453 SP; 260/453 AM
[58] Field of Search .................. 260/453 SP, 453 AM

[56] References Cited

U.S. PATENT DOCUMENTS

| | | | |
|---|---|---|---|
| 3,644,457 | 2/1972 | König et al. | 260/453 SP |
| 3,883,571 | 5/1975 | Allport et al. | 260/453 AM |
| 4,055,548 | 10/1977 | Carleton et al. | 260/453 SP X |
| 4,115,429 | 9/1978 | Leiff et al. | 260/453 SP |
| 4,118,411 | 10/1978 | Leiff et al. | 260/453 SP |
| 4,229,347 | 10/1980 | Holt et al. | 260/239 A |

*Primary Examiner*—Dolph H. Torrence
*Attorney, Agent, or Firm*—Gene Harsh; Joseph C. Gil

[57] ABSTRACT

The present invention is directed to a process for the preparation of a stable, liquid adduct comprising reacting a mixture of 1,3-butane diol and neopentyl glycol with diphenylmethane diisocyanate at a temperature of from about 25° C. to about 120° C. in an amount such that said adduct has an isocyanate group content of from about 20 to about 30 percent by weight, and wherein the ratio of mole equivalents of 1,3-butane diol to mole equivalents of neopentyl glycol is from 0.05:0.95 to 0.95:0.05, with the further proviso that (i) if the 4,4'-isomer content of the diphenylmethane diisocyanate is equal to or greater than 98 percent by weight, then said ratio is from 0.30:0.70 to 0.65:0.35, (ii) if the 4,4'-isomer content of the diphenylmethane diisocyanate is less than 98 percent by weight but not less than 90 percent by weight, then said ratio is from 0.30:0.70 to 0.75:0.25, (iii) if the 4,4'-isomer content of the diphenylmethane diisocyanate is less than 90 percent by weight but not less than 80 percent by weight, then said ratio is from 0.30:0.70 to 0.85:0.15 and (iv) if the 4,4'-isomer content of the diphenylmethane diisocyanate is less than 80 percent by weight but not less than 65 percent by weight, then said ratio is from 0.30:0.70 to 0.95:0.05.

The invention is also directed to a product produced from such process.

11 Claims, No Drawings

LIQUID DIPHENYLMETHANE DIISOCYANATE COMPOSITIONS

The present invention relates to the preparation of organic isocyanates based on 2,2'-, 2,4'- and/or 4,4'-diphenylmethane diisocyanates which are liquid at room temperature and to the products so-produced.

BACKGROUND OF THE INVENTION

It is well known that diisocyanates which are liquid at room temperature have numerous advantages over solid diisocyanates because they are easier to mix and to work with. Diisocyanates, which are liquid at room temperature, and which find wide commercial use, such as toluene diisocyanate or hexamethylene diisocyanate, are, as a rule, physiologically harmful because of their high vapor pressure and can only be handled if certain safety precautions are taken. For this reason, various attempts have been made to convert diisocyanates that are solid at room temperature into the liquid form.

The most important diisocyanates which are solid at room temperature, and which are readily available on a large commercial scale, are 4,4'-diphenylmethane diisocyanate and the 2,4'-isomer thereof, which melt at 39° C. and 34.5° C., respectively. Attempts have been made to liquify the 4,4'-diphenylmethane diisocyanate isomer. Thus, 4,4'-diphenylmethane diisocyanate was heated to temperatures above 150° C., to affect a partial carbodiimization of the isocyanate according to U.S. Pat. No. 3,152,162. The isocyanate groups still present partly react with the resulting carbodiimide groups to form uretone imine, resulting in liquid polyisocyanates, rather than liquid diisocyanates.

It is also known from U.S. Pat. No. 3,644,457 to react 4,4'- and/or 2,4'-diphenylmethane diisocyanate with a branched aliphatic dihydroxy compound or polyethers based on 1,2-propylene glycol to produce a product which is liquid at room temperature. According to this reference, 1 mole of a diphenylmethane diisocyanate is reacted with from about 0.1 to about 0.3 moles of the branched aliphatic dihydroxy compound or the poly-1,2-propylene ether glycol. In a similar manner, U.S. Pat. No. 4,055,548 teaches that diphenylmethane diisocyanates can be liquified by reaction with ethylene glycol-based polyethers.

Liquid diphenylmethane diisocyanates have been produced by reacting diisocyanates having specified 2,4'-isomer contents with propylene and polypropylene glycols and with polyoxyethylene glycols (see, e.g., U.S. Pat. Nos. 4,118,411 and 4,115,429).

It has also been proposed to prepare liquid diphenylmethane diisocyanate compositions by reacting the diisocyanates with three separate alkylene glycols, each having at least three carbon atoms (see, e.g., U.S. Pat. No. 3,883,571), or by reacting the diisocyanate with at least three separate alkylene glycols, each having at least three carbon atoms, and wherein at least one of the glycols is dipropylene, tripropylene, or polypropylene glycol (see, e.g., U.S. Pat. No. 4,229,347).

Even though it is known to use various dihydroxy compounds as described above to prepare liquid isocyanates, is has not been possible to prepare such adducts using readily available, inexpensive dihydroxy compounds.

It is therefore an object of this invention to provide organic isocyanates which are liquid at room temperature and which remain liquid without formation of gel particles even after prolonged storage at room temperature.

DESCRIPTION OF THE INVENTION

The present invention is directed to a process for the preparation of stable, liquid adducts of diphenylmethane diisocyanate and to the adducts so-produced. The process broadly comprises reacting a mixture of 1,3-butane diol and neopentyl glycol with diphenylmethane diisocyanate at a temperature of from about 25° C. to about 120° C. in an amount such that the resultant product has an isocyanate group content of from about 20 to about 30 percent by weight, wherein the ratio of mole equivalents of 1,3-butane diol to mole equivalents of neopentyl glycol is from 0.05:0.95 to 0.95:0.05, with the further proviso that (i) if the 4,4'-isomer content of the diphenylmethane diisocyanate is equal to or greater than 98 percent by weight, then said ratio is from 0.30:0.70 to 0.65:0.35, (ii) if the 4,4'-isomer content of the diphenylmethane diisocyanate is less than 98 percent by weight but not less than 90 percent by weight, then said ratio is from 0.30:0.70 to 0.75:0.25, (iii) if the 4,4'-isomer content of the diphenylmethane diisocyanate is less than 90 percent by weight but not less than 80 percent by weight, then said ratio is from 0.30:0.70 to 0.85:0.15 and (iv) if and 4,4'-isomer content of the diphenylmethane diisocyanate is less than 80 percent by weight but not less than 65 percent by weight, then said ratio is from 0.30:0.70 to 0.95:0.05.

As used herein, the term "diphenylmethane diisocyanate" is defined as being 4,4'-diphenylmethane diisocyanate, 2,4'-diphenylmethane diisocyanate, 2,2'-diphenylmethane diisocyanate and mixtures thereof. In addition, "stable, liquid adducts" are those which are liquid at ambient temperature and remain liquid without the formation of gel particles after storage at ambient temperature.

Most short chain diols, such as 1,4-butane diol, 1,3-butane diol, 1,3-propylene glycol, 1,2-propylene glycol, ethylene glycol and neopentyl glycol result in solids at ambient temperatures when reacted with diphenylmethane diisocyanate to produce adducts which have NCO contents of about 20 to 30%. Therefore, it was surprising that the reaction of specific mixtures of 1,3-butane diol and neopentyl glycol to produce adducts with diphenylmethane diisocyanate, resulted in adducts that were liquid and remained liquid after storage at ambient temperature.

The diphenylmethane diisocyanate which is used as a reactant in accordance with the process of the present invention preferably contains from about 30 to 100% by weight of 4,4'-diphenylmethane diisocyanate, from 0 to about 70% by weight of 2,4'-diphenylmethane diisocyanate and from 0 to about 10% by weight of 2,2'-diphenylmethane diisocyanate. The diphenylmethane diisocyanate is reacted with the mixture of diols at temperatures of from about 25° to 120° C., preferably from about 40° to 100° C., and most preferably from about 60° to 80° C. The lower temperatures are generally preferred since they help to eliminate allophanate formation from the formed urethane groups and excess diisocyanate.

The amounts of diol mixture and diphenylmethane diisocyanate are chosen such that the liquid adduct has an isocyanate group content of from about 20 to 30%, preferably from about 21 to 27% by weight. Generally, in order to yield such an isocyanate group content the equivalent ratio of isocyanate to hydroxyl groups is from about 3:1 to 13:1 and preferably about 3:1 to 7:1. The liquid adduct may also be prepared as a concentrate, i.e., with a lower NCO content, and subsequently diluted with additional diphenylmethane diisocyanate to adjust the NCO content to the desired value.

The process for preparing the liquid adduct may be carried out by introducing the mixture of dihydroxy compounds into the diisocyanate or by introducing the diisocyanate into the mixture of dihydroxy compounds. The former method is preferred. Regardless of which method of addition is used, it is generally recommended to maintain the reactants at the previously discussed temperatures with stirring.

The ratio of mole equivalents of the two dihydroxy compounds which is necessary to prepare a liquid adduct is generally dependent upon the 4,4'-isomer content of the diphenylmethane diisocyanate reactant. Generally, the ratio of mole equivalents of 1,3-butane diol to mole equivalents of neopentyl glycol is from 0.5:0.95 to 0.95:0.05. These ratios will vary according to the 4,4'-isomer content of the diphenylmethane diisocyanate. If the 4,4'-isomer content of the diphenylmethane is equal to or greater than 98 percent by weight, the ratio should be from 0.30:0.70 to 0.65:0.35. If the 4,4'-isomer content is less than 98 percent by weight but no less than 90 percent by weight, the ratio should be from 0.30:0.70 to 0.75:0.25. If the 4,4'-isomer content of diphenylmethane diisocyanate is less than 90 percent by weight but not less than 80 percent by weight, then the ratio should be from 0.30:0.70 to 0.85:0.15. If the 4,4'-isomer content of the diphenylmethane diisocyanate is less than 80 percent by weight but not less than 65 percent by weight, then the ratio should be from 0.30:0.70 to 0.95:0.05. Regardless of the 4,4'-isomer content, the presently preferred ratio is from 0.40:0.60 to 0.60:0.40.

The liquid adducts of the present invention may be used in various polyaddition reactions in the coatings, plastics and foam industries. For example, they may be used in the production of polyurethane foams, polyurethane elastomers such as shoe soles, etc. or for the production of elastomers or plastics by the RIM process.

The invention is further illustrated, but is not intended to be limited by the following examples in which all parts and percentages are by weight unless otherwise specified.

EXAMPLES

In the examples which follow, the isocyanates and diol mixtures used were those set forth in TABLES 1 and 2, respectively.

TABLE 1

| Isocyanate Type | ISOCYANATES Diphenylmethane Diisocyanate | | |
|---|---|---|---|
| | Percent by weight 4,4'-isomer | Percent by weight 2,4'-isomer | Percent by weight 2,2'-isomer |
| A | 98 | 2 | 0 |
| B | 90 | 10 | 0 |
| C | 80 | 19 | 1 |
| D | 70 | 29 | 1 |
| E | 66 | 33 | 1 |
| F | 65 | 34 | 1 |
| G | 56 | 38 | 6 |
| H | 45 | 53 | 2 |

TABLE 2

| Diol Type | DIOLS | | |
|---|---|---|---|
| | Mole Equivalents 1,3-butane diol | Mole Equivalents neopentyl glycol | Mole Equivalent Ratio |
| I | 1.0 | — | — |
| II | 0.10 | 0.90 | 0.10:0.90 |
| III | 0.25 | 0.75 | 0.25:0.75 |
| IV | 0.40 | 0.60 | 0.40:0.60 |
| V | 0.50 | 0.50 | 0.50:0.50 |
| VI | 0.60 | 0.40 | 0.60:0.40 |
| VII | 0.70 | 0.30 | 0.70:0.30 |
| VIII | 0.75 | 0.25 | 0.75:0.25 |
| IX | 0.90 | 0.10 | 0.90:0.10 |
| X | — | 1.0 | — |

In preparing the various diol blends in TABLE 2, the butane diol was added to the neopentyl glycol and the mixture was warmed to about 85° C. until all the neopentyl glycol went into solution.

Adducts were then prepared by introducing the various diol types into the various isocyanate types with stirring. The mixture was maintained at a specific temperature for a specific time. The type and amount of isocyanate, the type and amount of diol, the times and temperatures were as specified in TABLE 3. The isocyanate group contents of the products, the viscosities of the products and the appearance of the products after storage for seven (7) days at 25° C. were as indicated in TABLE 3.

Examples 1 through 24 represent embodiments of the present invention, while Examples 25 through 40 represent comparison examples. In the table, NR means "not recorded".

TABLE 3

| Example | Isocyanate | | | Diol | | | Time minutes | Temp. °C. | % by weight NCO groups | Viscosity at 25° C. M.Pa.s | Appearance after 7 days at 25° C. |
|---|---|---|---|---|---|---|---|---|---|---|---|
| | Type | % by weight 4,4'-content | Parts by weight | Type | Ratio of mole Equivalents | Parts by weight | | | | | |
| 1 | A | 98 | 503 | IV | 0.40:0.60 | 49 | 20 | 80 | 22.7 | 1720 | liquid |
| 2 | B | 90 | 503 | IV | 0.40:0.60 | 49 | 20 | 80 | 22.8 | 1920 | liquid |
| 3 | C | 80 | 503 | IV | 0.40:0.60 | 49 | 20 | 80 | 22.8 | 2080 | liquid |
| 4 | D | 70 | 503 | IV | 0.40:0.60 | 49 | 20 | 80 | 22.7 | 2320 | liquid |
| 5 | A | 98 | 517 | V | 0.50:0.50 | 50 | NR | NR | 22.8 | 2230 | liquid |
| 6 | E | 66 | 1001 | V | 0.50:0.50 | 97 | 50 | 70 | 23.0 | 2550 | liquid |
| 7 | A | 98 | 500 | VI | 0.60:0.40 | 48 | 15 | 75 | 22.9 | 1840 | liquid |
| 8 | B | 90 | 500 | VI | 0.60:0.40 | 48 | 15 | 75 | 22.8 | 2080 | liquid |
| 9 | C | 80 | 500 | VI | 0.60:0.40 | 48 | 15 | 75 | 23.0 | 2240 | liquid |
| 10 | B | 90 | 500 | VII | 0.70:0.30 | 47 | 15 | 70 | 22.8 | 1820 | liquid |
| 11 | C | 80 | 500 | VII | 0.70:0.30 | 47 | 15 | 70 | 23.0 | 2060 | liquid |
| 12 | E | 66 | 1001 | VIII | 0.75:0.25 | 94 | 30 | 65 | 23.0 | 2530 | liquid |
| 13 | F | 65 | 542 | IX | 0.90:0.10 | 50 | 15 | 80 | 23.0 | 2800 | liquid |
| 14 | F | 65 | 1001 | IX | 0.90:0.10 | 92 | 35 | 68 | 23.0 | 3050 | liquid |
| 15 | G | 56 | 1002 | IX | 0.90:0.10 | 92 | 35 | 70 | 23.0 | NR | liquid |
| 16 | H | 45 | 1002 | IX | 0.90:0.10 | 92 | 35 | 68 | 23.0 | 2580 | liquid |

TABLE 3-continued

| Example | Isocyanate Type | Isocyanate % by weight 4,4'-content | Isocyanate Parts by weight | Diol Type | Diol Ratio of mole Equivalents | Diol Parts by weight | Time minutes | Temp., °C. | % by weight NCO groups | Viscosity at 25° C. M.Pa.s | Appearance after 7 days at 25° C. |
|---|---|---|---|---|---|---|---|---|---|---|---|
| 17 | A | 98 | 414 | V | 0.50:0.50 | 50 | 15 | 80 | 21.0 | 9700 | liquid |
| 18 | A | 98 | 631 | IV | 0.40:0.60 | 49 | 15 | 80 | 25.0 | 240 | liquid |
| 19 | A | 98 | 630 | V | 0.50:0.50 | 50 | 15 | 75 | 24.9 | 380 | liquid |
| 20 | E | 66 | 1001 | V | 0.50:0.50 | 77 | 35 | 70 | 25.0 | 530 | liquid |
| 21 | A | 98 | 627 | VI | 0.60:0.40 | 48 | 15 | 70 | 24.9 | 430 | slightly turbid liquid |
| 22 | E | 66 | 1001 | VII | 0.70:0.30 | 75 | 35 | 70 | 25.0 | NR | liquid |
| 23 | E | 66 | 1001 | IX | 0.90:0.10 | 73 | 25 | 70 | 25.0 | NR | liquid |
| 24 | A | 98 | 835 | V | 0.50:0.50 | 48 | 15 | 70 | 27.1 | 110 | liquid |
| 25 | A | 98 | 1200 | I | — | 90 | 15 | 70 | 24.6 | | solid |
| 26 | A | 98 | 1207 | X | — | 104 | 15 | 70 | 24.4 | | solid |
| 27 | F | 65 | 509 | X | — | 52 | 15 | 70 | 22.8 | 1980 | slightly turbid liquid |
| 28 | A | 98 | 495 | II | 0.10:0.90 | 50 | 15 | 70 | 23.0 | | solid |
| 29 | C | 80 | 495 | II | 0.10:0.90 | 50 | 15 | 70 | 22.7 | | solid |
| 30 | D | 70 | 495 | II | 0.10:0.90 | 50 | 15 | 80 | 23.0 | 1880 | liquid with gel particles |
| 31 | F | 65 | 495 | II | 0.10:0.90 | 50 | 15 | 80 | 22.9 | 1800 | slightly turbid liquid |
| 32 | A | 98 | 505 | III | 0.25:0.75 | 50 | 15 | 75 | 23.0 | | solid |
| 33 | B | 90 | 505 | III | 0.25:0.75 | 50 | 15 | 75 | 23.0 | | gel |
| 34 | C | 80 | 505 | III | 0.25:0.75 | 50 | 15 | 75 | 22.9 | | liquid with gel particles |
| 35 | D | 70 | 505 | III | 0.25:0.75 | 50 | 15 | 75 | 22.6 | 2640 | slightly turbid liquid |
| 36 | A | 98 | 500 | VII | 0.70:0.30 | 47 | 15 | 70 | 22.9 | 1776 | slightly turbid liquid |
| 37 | A | 98 | 542 | IX | 0.90:0.10 | 50 | 30 | 65 | 23.0 | | solid |
| 38 | B | 90 | 542 | IX | 0.90:0.10 | 50 | 20 | 80 | 23.0 | | solid |
| 39 | C | 80 | 542 | IX | 0.90:0.10 | 50 | 15 | 70 | 22.9 | 1300 | slightly turbid liquid |
| 40 | D | 70 | 494 | I | — | 45 | 15 | 75 | 22.7 | 2880 | slightly turbid liquid |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a stable, liquid adduct comprising reacting a mixture of 1,3-butane diol and neopentyl glycol with diphenylmethane diisocyanate at a temperature of from about 25° C. to about 120° C. in an amount such that said adduct has an isocyanate group content of from about 20 to about 30 percent by weight, and wherein the ratio of mole equivalents of 1,3-butane diol to mole equivalents of neopentyl glycol is from 0.05:0.95 to 0.95:0.05, with the further proviso that
   (i) if the 4,4'-isomer content of the diphenylmethane diisocyanate is equal to or greater than 98 percent by weight, then said ratio is from 0.30:0.70 to 0.65:0.35,
   (ii) if the 4,4'-isomer content of the diphenylmethane diisocyanate is less than 98 percent by weight but not less than 90 percent by weight, then said ratio is from 0.30:0.70 to 0.75:0.25,
   (iii) if the 4,4'-isomer content of the diphenylmethane diisocyanate is less than 90 percent by weight but not less than 80 percent by weight, then said ratio is from 0.30:0.70 to 0.85:0.15, and
   (iv) if the 4,4'-isomer content of the diphenylmethane diisocyanate is less than 80 percent by weight but not less than 65 percent by weight, then said ratio is from 0.30:0.70 to 0.05:0.05.

2. The process of claim 1 wherein said diphenylmethane diisocyanate contains from about 30 to 100 percent by weight of the 4,4'-isomer, from 0 to about 70 percent by weight of the 2,4'-isomer, and from 0 to about 10 percent by weight of the 2,2'-isomer.

3. The process of claim 1, wherein said temperature is from about 40° C. to about 100° C.

4. The process of claim 3, wherein said temperature is from about 60° C. to about 80° C.

5. The process of claim 1, wherein said adduct has an isocyanate group content of from about 21 to 27 percent by weight.

6. The process of claim 1, wherein the equivalent ratio of isocyanate to hydroxyl groups is from about 3:1 to 13:1.

7. The process of claim 6 wherein said equivalent ratio is from about 3:1 to 7:1.

8. The process of claim 1 wherein said ratio is from 0.40:0.60 to 0.60:0.40.

9. The product of the process of claim 1.

10. The product of the process of claim 5.

11. The product of the process of claim 8.

* * * * *